United States Patent [19]

Tanaka et al.

[11] Patent Number: 4,797,506

[45] Date of Patent: Jan. 10, 1989

[54] 6-SUBSTITUTED PROSTAGLANDINS $E_1$ AND PROCESS FOR PRODUCING SAME

[75] Inventors: Toshio Tanaka; Atsuo Hazato, both of Hino; Seizi Kurozumi, Kokubunji, all of Japan

[73] Assignee: Teijin Limited, Osaka, Japan

[21] Appl. No.: 794,857

[22] PCT Filed: Feb. 28, 1985

[86] PCT No.: PCT/JP85/00096

§ 371 Date: Oct. 18, 1985

§ 102(e) Date: Oct. 18, 1985

[87] PCT Pub. No.: WO85/03935

PCT Pub. Date: Sep. 12, 1985

[30] Foreign Application Priority Data

Feb. 29, 1984 [JP] Japan ............... 59-36096

[51] Int. Cl.$^4$ .......................... C07D 177/00
[52] U.S. Cl. ...................... 560/121; 549/422; 549/466; 556/441; 560/53; 560/118; 562/463; 562/500; 562/503
[58] Field of Search ............ 514/530; 560/121, 53, 560/118; 562/503, 463, 500; 549/422, 466; 556/441

[56] References Cited

U.S. PATENT DOCUMENTS 4,649,156 3/1987 Tanaka .................. 514/530

FOREIGN PATENT DOCUMENTS

| 5444639 | 4/1979 | Japan | 560/121 |
| 55141465 | 11/1980 | Japan | 560/121 |
| 5936657 | 2/1981 | Japan | 514/530 |
| 5936658 | 2/1981 | Japan | 514/530 |

*Primary Examiner*—Robert Gerstl
*Attorney, Agent, or Firm*—Kenyon & Kenyon

[57] ABSTRACT

6-substituted prostaglandins $E_1$ which are compounds represented by the following formula [I] or their enantiomers or mixtures whereof in any ratio:

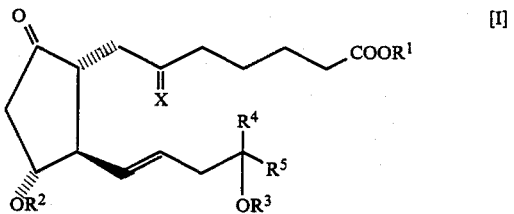

wherein $R^1$ represents a hydrogen atom, a $C_1$–$C_{16}$ alkyl group, a substituted or unsubstituted phenyl group, a substituted or unsubstituted phenyl $C_3$–$C_{10}$ cycloalkyl group, a substituted or unsubstituted phenyl ($C_1$–$C_2$) alkyl group, or one equivalent cation; $R^2$ and $R^3$, which may be the same or different, represent a hydrogen atom, a tri ($C_1$–$C_7$) hydrocarbon silyl group, or a group forming an acetal linkage together with an oxygen atom of a hydroxyl group; $R^4$ represents a hydrogen atom, a methyl group or a vinyl group; $R^5$ represents a linear or branched $C_3$–$C_8$ alkyl group, a linear or branched $C_3$–$C_8$ alkenyl group, a linear or branced $C_3$–$C_8$ alkynyl group, a phenyl group which may be substituted, a phenoxy group which may be substituted, a $C_3$–$C_{10}$ cycloalkyl group which may be substituted, or a linear or branched $C_1$–$C_5$ alkyl group which may be substituted with a $C_1$–$C_6$ alkoxy group, a phenyl group which may be substituted, a phenoxy group which may be substituted, or a $C_3$–$C_{10}$ cycloalkyl group which may be substituted; and X represents an

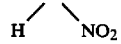

group or an oxygen atom.

Such 6-substituted prostaglandins $E_1$ are useful for the treatment and/or prevention of digestive organ diseases such as duodenal ulcers or gastric ulcers.

4 Claims, No Drawings

...

6-SUBSTITUTED PROSTAGLANDINS $E_1$ AND PROCESS FOR PRODUCING SAME

DESCRIPTION

1. Technical Field

The present invention relates to 6-substituted prostaglandins $E_1$ and a process for producing the same. More specifically, the present invention relates to 6-substituted prostaglandins $E_1$ such as 6-nitroprostaglandins $E_1$ and 6-oxoprostaglandins $E_1$, which are useful as a medicine for the treatment of duodenal ulcers, gastric ulcers, etc., and an industrially advantageous process for producing 6-substituted prostaglandins $E_1$ wherein organolithium compounds, copper compounds, 4-substituted-2-cyclopentenones, and nitroolefins are used.

2. Background Art 6-oxoprostaglandin $E_1$ has a platelet aggregation inhibition effect and a hypertensive effect due to a smooth muscle relaxing effect which are as strong as those of prostacyclin, and is known as an active metabolite of prostacyclin in vivo (C. P. Quilley et al., European Journal of Pharmacology, vol. 57, pp. 273–276, 1979; P. Y. K. Wong et al, European Journal of Pharmacology, vol. 60, pp. 245–248, 1979; C. N. Berry et al., Pharmacology, vol. 26, pp. 324–330, 1983; and R. J. Griffiths et al., British Journal of Pharmacology, vol. 79, pp. 149–155, 1983). It is known that some analogues of 6-oxoprostaglandin $E_1$ have not only a platelet aggregation inhibition effect and a hypertensive effect but also an excellent antiulcerative effect (Japanese Unexamined Patent Publication Nos. 54-44639 and 55-141465).

On the other hand, prostacyclin exhibits a half-life of activity on the order of several minutes at a physiological pH, and thus, is unstable, as a medicine. However, the above-mentioned 6-oxoprostaglandin $E_1$ is more stable than prostacyclin (C. P. Quilley et al., European Journal of Pharmacology, vol 57, pp. 273–276, 1979). Thus, there is a desire in the field for the application of 6-oxoprostaglandin $E_1$ and its analogues as a medicine.

Moreover, 6-nitroprostaglandins $E_1$ are known and have pharmacological effects such as a platelet aggregation inhibition effect (Japanese Unexamined Patent Publication No. 59-36657).

Conventionally, the above-mentioned 6-oxoprostaglandin $E_1$ analogues are prepared through prostacyclin by means of several process using, as the starting material, prostaglandin $F_{2\alpha}$ and its analogues, which are obtained through an intermediate referred to as a so-called corey lactone (Japanese Unexamined Patent Publication Nos. 54-44639 and 55-141465). However, this production process not only requires many process to obtain the desired compound but also the resultant derivative is only a compound having a hydroxyl group at the 15-position according to the prostaglandin nomenclature. Therefore, this process is disadvantageous in that it is deficient in general-purpose properties.

DISCLOSURE OF THE INVENTION

An object of the present invention is to provide a novel 15-deoxy-16-hydroxy-6-oxoprostaglandins $E_1$ and a novel 15-deoxy-16-hydroxy-6-nitroprostaglandins $E_1$ wherein the hydroxyl group at the 15-position of natural type prostaglandin is shifted to the 16-position.

Another object of the present invention is to provide a novel 6-substituted prostaglandins $E_1$, such as a novel 15-deoxy-16-hydroxy-6-nitroprostaglandins $E_1$ and 15-deoxy-16-hydroxy-6-oxoprostaglandins $E_1$, which are useful for the treatment of digestive organ diseases such as duodenal ulcers and gastric ulcers.

Still another object of the present invention is to provide a process for producing 6-substituted prostaglandins $E_1$ which is extremely excellent for industrial purposes.

Other objects and advantages of the present invention will be apparent from the following description.

The objects and advantages of the present invention are attained by the following 6-substituted prostaglandins $E_1$.

That is, the present invention is 6-substituted prostaglandins $E_1$, which are compounds represented by the following formula [I] or their enantiomers or mixtures thereof in any ratio:

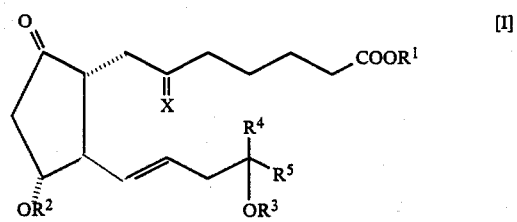

wherein $R^1$ represents a hydrogen atom, a $C_1$–$C_{10}$ alkyl group, a substituted or unsubstituted phenyl group, a substituted or unsubstituted $C_3$–$C_{10}$ cycloalkyl group, a substituted or unsubstituted phenyl ($C_1$–$C_2$) alkyl group, or one equivalent cation; $R^2$ and $R^3$, which may be the same or different, represent a hydrogen atom, a tri ($C_1$–$C_7$) hydrocarbon silyl group, or a group forming an acetal linkage together with an oxygen atom of a hydroxyl group; $R^4$ represents a hydrogen atom, a methyl group or a vinyl group; $R^5$ represents a linear or branched $C_3$–$C_8$ alkyl group, a linear or branched $C_3$–$C_8$ alkenyl group, a linear or branched $C_3$–$C_8$ alkynyl group, a phenyl group which may be substituted, a phenoxy group which may be substituted, a $C_3$–$C_{10}$ cycloalkyl group which may be substituted, or a linear or branched $C_1$–$C_5$ alkyl group which may be substituted with a $C_1$–$C_6$ alkoxy group, a phenyl group which may be substituted, a phenoxy group which may be substituted, or a $C_3$–$C_{10}$ cycloalkyl group which may be substituted; and X represents an

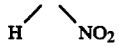

group or an oxygen atom.

BEST MODE FOR CARRYING OUT THE INVENTION

In the formula [I], X represents an

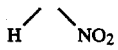

group or an oxygen atom. Therefore, when X represents an

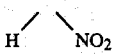

group, the formula (1) signifies 6-nitroprostaglandins $E_1$ of the formula [I-1]:

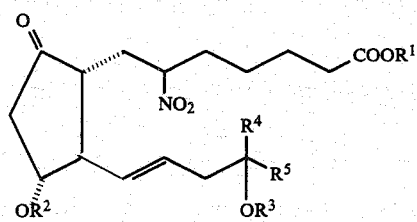

wherein
$R_1$, $R^2$, $R^3$, $R^4$ and $R^5$ are the same as defined above.

When X represents an oxygen atom, the formula [I] signifies 6-oxoprostaglandins $E_1$ of the formula [I-2]:

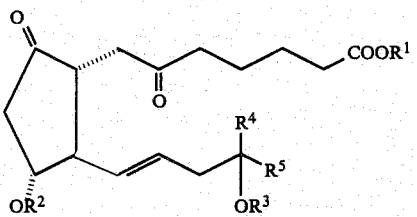

wherein
$R^1$, $R^2$, $R^3$, $R^4$ and $R^5$ are the same as defined above.

$R^1$ represents a hydrogen atom, a $C_1$–$C_{10}$ alkyl group, a substituted or unsubstituted phenyl group, a substituted or unsubstituted $C_3$–$C_{10}$ cycloalkyl group, a substituted or unsubstituted phenyl ($C_1$–$C_2$) alkyl group, or one equivalent cation.

The $C_1$–$C_{10}$ alkyl groups may be lnear or branched and may include, for example, methyl, ethyl, n-proplyl, iso-propyl, n-butyl, sec-butyl, tert-butyl, n-pentyl, n-hexyl, n-heptyl, n-octyl, n-nonyl, and n-decyl.

The substituent of the substituted phenyl is preferably, for example, a halogen atom, a hydroxy group, a $C_2$–$C_7$ acyloxy group, a $C_1$–$C_4$ alkyl group which may be substituted with a halogen atom, a $C_1$–$C_4$ alkoxy group which may be substituted with a halogen atom, a nitrile group, a carboxyl group or a ($C_1$–$C_6$) alkoxycarbonyl group. The halogen atom is, for example, fluorine, chlorine or bromine, and particularly preferably, fluorine or chlorine. The $C_2$–$C_7$ acyloxy group may include, for example, acetoxy, propionyloxy, n-butyryloxy, iso-butyryloxy, n-valeryloxy, iso-valeryloxy, caproyloxy, enanthyloxy or benzoyloxy.

The $C_1$–$C_4$ alkyl groups which may be substituted with a halogen may preferably include, for example, methyl, ethyl, n-propyl, iso-propyl, n-butyl, chloromethyl, dichloromethyl, and trifluoromethyl. The $C_1$–$C_4$ alkoxy groups which may be substituted with a halogen may preferably include, for example, methoxy, ethoxy, n-propoxy, iso-propoxy, n-butoxy, chloromethoxy, dichloromethoxy and trifluoromethoxy. The ($C_1$–$C_6$) alkoxycarbonyl groups may include, for example, methoxycarbonyl, ethoxycarbonyl, butoxycarbonyl and hexyloxycarbonyl.

The substituted phenyl group may have 1 to 3, preferably one, substituents as mentioned above.

The substituted or unsubstituted $C_3$–$C_{10}$ cycloalkyl group may be substituted with a similar substituent as mentioned above or may be a unsubstituted $C_3$–$C_{10}$, preferably $C_5$–$C_6$, cycloalkyl group, such as cyclopropyl, cyclopentyl, cyclohexenyl, cycloheptyl, cyclooctyl, and cyclodecyl.

The substituted or unsubstituted phenyl ($C_1$–$C_2$) alkyl groups may be substituted with a similar substituent as mentioned above or may include, for example, unsubstituted benzyl, α-phenethyl and β-phenethyl.

The equivalent cations may include, for example, ammonium cation such as tetramethylammonium, monomethylammonium, dimethylammonium, trimethylammonium, benzylammonium, phenethylammonium, morpholinium cation, monoethanolammonium and piperidinium cation; alkali metal cations such as $Na^+$ and $K^+$; and divalent or trivalent metal cations such as $\frac{1}{2} Ca^{2+}$, $\frac{1}{2} Mg^{2+}$, $\frac{1}{2} Zn^{2+}$ and $\frac{1}{3} Al^{3+}$.

$R^1$ is preferably a hydrogen atom, a $C_1$–$C_{10}$ alkyl group or one equivalent cation.

$R^2$ and $R^3$ may be the same or different and represent a hydrogen atom, a tri ($C_1$–$C_7$) hydrocarbon silyl group or a group forming an acetal linkage together with an oxygen atom of a hydroxyl group.

The tri ($C_1$–$C_7$) hydrocarbon silyl group may preferably include, for example, a tri ($C_1$–$C_4$) alkylsilyl such as trimethylsilyl, triethylsilyl, and t-butyldimethylsilyl; a diphenyl ($C_1$–$C_4$) alkylsilyl such as t-butyldiphenylsilyl or tribenzylsilyl.

The groups forming an acetal linkage together with an oxygen atom of a hydroxyl group may include, for example, methoxyethyl, 1-ethoxyethyl, 2-methoxy-2-propyl, 2-ethoxy-2-propyl, (2-methoxyethoxy) methyl, benzyloxymethyl, 2-tetrahydropyranyl, 2-tetrahydrofuranyl or 6,6-dimethyl-3-oxa-2-oxobicyclo [3.1.0] hex-4-yl. Of these, 2-tetrahydropyranyl, 2-tetrahydrofuranyl, 1-ethoxyethyl, 2-methoxy-2-propyl, (2-methoxyethoxy) methyl, or 6,6-dimethyl-3-oxa-2-oxobicyclo [3.1.0] hex-4-yl is especially preferable.

As $R^2$ or $R^3$, among the above-mentioned groups, a hydrogen atom, a tri ($C_1$–$C_4$) alkylsilyl group, a diphenyl ($C_1$–$C_4$) alkylsilyl group, a 2-tetrahydropyranyl group, a 2-tetrahydrofuranyl group, an 1-ethoxyethyl group, a 2-ethoxy-2-propyl group, a (2-methoxyethoxy) methyl group or a 6,6-dimethyl-3-oxa-2-oxobicyclo 3.1.0 hex-4-yl group is preferable.

In the formula [I] (including [I-1] and [I-2]), $R^4$ represents a hydrogen atom, a methyl group or a vinyl group.

In the formula [I] (including [I-1] and [I-2]), $R^5$ represents a linear or branched $C_3$–$C_8$ alkyl group a linear or branched $C_3$–$C_8$ alkenyl group, a linear or branched alkynyl group, a phenyl group which may be substituted, a phenoxy group which may be substituted, a $C_3$–$C_{10}$ cycloalkyl group which may be substituted, or a linear or branched $C_1$–$C_5$ alkyl group which may be substituted with a $C_1$–$C_6$ alkoxy group, a phenyl group which may be substituted, a phenoxy group which may be substituted or a $C_3$–$C_{10}$ cycloalkyl group which may be substituted.

The linear or brahced $C_3$–$C_8$ alkyl groups may include n-propyl, n-butyl n-pentyl, n-hexyl, 1-methyl-1-butyl, and 2-methyl-1-butyl, preferably n-butyl, n-pentyl, and 1-methyl-1-butyl, particularly preferably, butyl.

The linear or brached $C_3$–$C_8$ alkenyl groups may include, for example, 1-butenyl, 2-butenyl and 1-pentenyl. The linear or branched $C_3$–$C_8$ alkynyl groups may include 1-butynyl, 2-butynyl and 1-pentynyl.

The substituent of a phenyl group which may be substituted, a phenoxy group which may be substituted and a $C_3$-$C_{10}$ cycloalkyl group which may be substituted may be a similar substituent as mentioned for the substituent of a substituted phenyl group of $R^1$. The unsubstituted $C_3$-$C_7$ cycloalkyl group may include preferably a $C_4$-$C_7$, more preferably a $C_5$-$C_6$, cycloalkyl group, for example, cyclopropyl, cyclopentyl, cyclohexyl, cycloheptyl, cyclooctyl and cyclodecyl.

The $C_1$-$C_6$ alkoxy groups in the linear or branched $C_1$-$C_5$ alkyl group which may be substituted with a $C_1$-$C_6$ alkoxy group, a phenyl group which may be substituted, a phenoxy group which may be substituted on a $C_3$-$C_{10}$ cycloalkyl group which may be substituted may include, for example, methoxy, ethoxy, propoxy, isopropoxy, butoxy, t-butoxy, and hexyloxy. The phenyl group which may be substituted and the phenoxy group which may be substituted may preferably include those mentioned above. The $C_3$-$C_{10}$ cycloalkyl groups which may be substituted may preferably include those mentioned above. The linear or branched $C_1$-$C_5$ alkyl groups substituted with these groups may include, for example, methyl, ethyl, n-propyl, isopropyl, n-butyl, iso-butyl, sec-butyl, t-butyl and pentyl. The substituents may be attached to the alkyl group at any position.

As $R^5$, butyl, pentyl, 1-methyl-1-butyl, 2-methyl-1-butyl, cyclopentyl, cyclohexyl and phenyl are preferable.

In the compound of the formula [I], the configuration of a substituent attached on the cyclopentanone ring is the same as has natural prostaglandin $E_1$. Therefore, such a stereoisomer is especially useful. The present invention includes stereoisomers which are the enantiomer of the above-mentioned stereoisomer and have the following formula [I'], or mixtures thereof in any ratio:

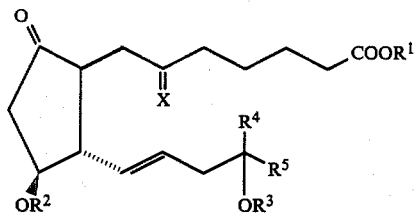

[I']

wherein
$R^1$, $R^2$, $R^3$, $R^4$, $R^5$ and X are the same as defined above.

Since the 16-position carbon to which a hydroxyl substituent, which may be protected, is attached is an asymmetric carbon atom, two types of optical isomers exist. The present invention includes any of these optical isomers or mixtures thereof in any ratio. In addition, when X represent an

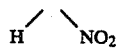

group, the carbon to which a nitro group is attached is an asymmetric carbon atom. In this case, similarly, two types of optical isomers exist. These optical isomers are prepared as a mixture thereof in substantially the same amounts in consideration of the production process as described hereinafter.

Preferable examples of the 6-substituted prostaglandins $E_1$ of the formula I which are provided by the present invention may include the following compounds.

(I) Examples of compounds in which X is an

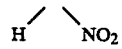

group
(01) 15-deoxy-16-hydroxy-6-nitoprostaglandin $E_1$
(02) 15-deoxy-16-hydroxy-18-oxa-6-nitroprostaglandin $E_1$
(03) 18,19,20-trinor-15-deoxy-16-hydroxy-17-phenoxy-6nitro-prostaglandin $E_1$
(04) 15-deoxy-16-hydroxy-20-methyl-6-nitroprostaglandin $E_1$
(05) 15-deoxy-16-hydroxy-17,20-dimethyl-6-nitroprostaglandin $E_1$
(06) 17,18,19,20-tetranor-15-deoxy-16-hydroxy-16-cyclopentyl-6-nitroprostaglandin $E_1$
(07) 17,18,19,20-tetranor-15-deoxy-16-hydroxy-16-cyclohexyl-6-nitroprostaglandin $E_1$
(08) 15-deoxy-16-hydroxy-16-methyl-6-nitroprostaglandin $E_1$
(09) 15-deoxy-16-hydroxy-16-methyl-18-oxa-6-nitrostaglandin $E_1$
(10) 18,19,20-trinor-15-deoxy-16-hydroxy-17-phenoxy-16-methyl-6-nitroprostaglandin $E_1$
(11) 15-deoxy-16-hydroxy-16,20-dimethyl-6-nitroprostaglandin $E_1$
(12) 15-deoxy-16-hydroxy-16,17,20-trimethyl-6-nitroprostaglandin $E_1$
(13) 17,18,19,20-tetranor-15-deoxy-16-hydroxy-16-cyclopentyl-16-methyl-6-nitroprostaglandin $E_1$
(14) 17,18,19,20-tetranor-15-deoxy-16-hydroxy-16-cyclohexyl-16-methyl-6-nitroprostaglandin $E_1$
(15) 15-deoxy-16-hydroxy-16-vinyl-6-nitroprostaglandin $E_1$
(16) 15-deoxy-16-hydroxy-16-vinyl-18-oxa-6-nitroprostaglandin $E_1$
(17) 18,19,20-trinor-15-deoxy-16-hydroxy-17-phenoxy-16-vinyl-6-nitroprostaglandin $E_1$
(18) 15-deoxy-16-hydroxy-20-methyl-16-vinyl-6-nitroprostaglandin $E_1$
(19) 15-deoxy-16-hydroxy-17,20-dimethyl-16-vinyl-6-nitroprostaglandin $E_1$
(20) 17,18,19,20-tetranor-15-deoxy-16-hydroxy-16-cyclopentyl-16-vinyl-6-nitroprostaglandin $E_1$
(21) 17,18,19,20-tetranor-15-deoxy-16-hydroxy-16-cyclohexyl-16-vinyl-6-nitroprostanglandin $E_1$
(22) The enantiomers of the compounds (01) to (22)
(23) The methyl esters of the compounds (01) to (22)
(24) The ethyl esters of the compounds (01) to (22)
(25) The sodium salts of the compounds (01) to (22)
(26) The ethers of the compounds (01) to (24) whose hydroxyl groups (at the 11- and 16-positions) are protected by a t-butyl-dimethylsilyl group and/or a 2-tetrahydropyranyl group.

The above-mentioned compounds are by no means limitative.

(II) Examples of compounds in which X is an oxygen atom
(31) 15-deoxy-16-hydroxy-6-oxoprostaglandin $E_1$

(32) 15-deoxy-16-hydroxy-18-oxa-6-oxoprostaglandin $E_1$
(33) 18,19,20-trinor-15-deoxy-16-hydroxy-17-phenoxy-6-oxo-prostaglandin $E_1$
(34) 15-deoxy-16-hydroxy-20-methyl-6-oxoprostaglandin $E_1$
(35) 15-deoxy-16-hydroxy-17,20-dimethyl-6-oxoprostaglandin $E_1$
(36) 17,18,19,20-tetranor-15-deoxy-16-hydroxy-16-cyclopentyl-6-oxoprostaglandin $E_1$
(37) 17,18,19,20-tetranor-15-deoxy-16-hydroxy-16-cyclohexyl-6-oxoprostaglandin $E_1$
(38) 15-deoxy-16-hydroxy-16-methyl-6-oxoprostaglandin $E_1$
(39) 15-deoxy-16-hydroxy-16-methyl-18-oxa-6-oxoprostaglandin $E_1$
(40) 18,19,20-trinor-15-deoxy-16-hydroxy-17-phenoxy-16-methyl-6-oxoprostaglandin $E_1$
(41) 15-deoxy-16-hydroxy-16,20-dimethyl-6-oxoprostaglandin $E_1$
(42) 15-deoxy-16-hydroxy-16,17,20-trimethyl-6-oxoprostaglandin $E_1$
(43) 17,18,19,20-tetranor-15-deoxy-16-hydroxy-16-cyclohexyl-16-methyl-6-oxoprostaglandin $E_1$
(44) 17,18,19,20-tetranor-15-deoxy-16-hydroxy-16-cyclohexyl-16-methyl-6-oxoprostaglandin $E_1$
(45) 15-deoxy-16-hydroxy-16-vinyl-6-oxoprostaglandin $E_1$
(46) 15-deoxy-16-hydroxy-16-vinyl-18-oxa-6-oxoprostaglandin $E_1$
(47) 18,19,20-trinor-15-deoxy-16-hydroxy-17-phenoxy-16-vinyl-6-oxoprostaglandin $E_1$
(48) 15-deoxy-16-hydroxy-20-methyl-16-vinyl-6-oxoprostaglandin $E_1$
(49) 15-deoxy-16-hydroxy-17,20-dimethyl-16-vinyl-6-oxoprostaglandin $E_1$
(50) 17,18,19,20-tetranor-15-deoxy-16-hydroxy-16-cyclopentyl-16-vinyl-6-oxoprostaglandin $E_1$
(51) 17,18,19,20-tetranor-15-deoxy-16-hydroxy-16-cyclohexyl-16-vinyl-6-oxoprostaglandin $E_1$
(52) The enantiomers of the compounds (31) to (51)
(53) The methyl esters of the compounds (31) to (52)
(54) The ethyl esters of the compounds (31) to (52)
(55) The sodium salt of the compounds (31) to (52)
(56) The ethers of the compounds (31) to (54) whose hydroxyl groups (at the 11- and 16-positions) are protected by a t-butyldimethylsilyl group and/or a 2-tetrahydropyranyl group.

The above-mentioned compounds are by no means limitative.

The 6-substituted prostaglandins $E_1$ of the formula [I-1] according to the present invention, wherein in the formula [I] is an

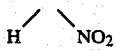

group, are prepared by reacting an organolithium compound of the formula [II]:

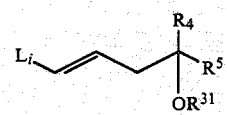

wherein
$R^4$ and $R^5$ are the same as defined above, and represents a tri ($C_1-C_7$) hydrocarbon silyl group or a group forming an acetal linkage together with an oxygen atom of a hydroxyl group,
with a copper compound of the formula [III]:

$$CuQ \qquad [III]$$

wherein
Q represents a halogen atom, a cyano group, a phenylthio group or a 1-pentyl group,
by then reacting the resultant product with 4-substituted-2-cyclopentenones of the formula [IV]:

wherein
$R^{21}$ represents a tri ($C_1-C_7$) hydrocarbon silyl group or a group forming an acetal linkage together with an oxygen atom of a hydroxyl group,
or the enantiomers thereof or mixtures thereof in any ratio, by reacting the resultant product with nitroolefins of the formula [V]:

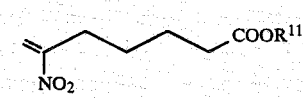

wherein
$R^{11}$ represents a $C_1-C_{10}$ alkyl group, a substituted or non-substituted phenyl group, a substituted or non-substituted $C_3-C_{10}$ cycloalkyl group, or a substituted or non-substituted phenyl ($C_1-C_2$) alkyl group,
and by optionally subjecting the resultant product to deprotection and/or hydrolysis and/or salt-formation reaction.

$R^{31}$ in the organolithium compound of the formula [II] which is the starting material of the present invention is defined as $R^3$ from which a hydrogen atom is removed. Such an organolithium compound is obtained, for example, by reacting the corresponding iodine compound with t-butyl lithium, etc., according to the following reaction formula:

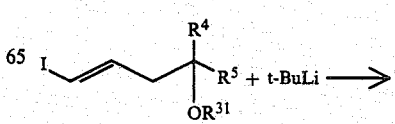

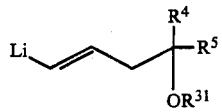

(J. Am. Chem. Soc., 94, 7210 (1972)).

Q in the copper compound of the formula [III] represents a halogen atom such as chlorine, fluorine, and bromine, a cyano group, a phenylthio group or a 1-pentyl group.

The reaction of the organolithium compound of the formula [II] with the copper compound of the formula [III] is usually carried out in the presence of an organic medium. Inert non-protonic organic media which are liquid under the reaction temperature and do not react with the reaction agents are used.

Such non-protonic inert organic media may include, for example, saturated hydrocarbons such as pentane, hexane and heptane; aromatic hydrocarbons such as benzene, toluene and xylene; ether solvents such as diethyl ether, tetrahydrofuran, dioxane, dimethoxyethane, and diethylene glycol dimethyl ether; and ether so-called non-protonic polar solvents such as hexamethylphosphorictriamide (HMP), N,N-dimethylformamide (DMF), N,N-dimethylacetamide (DMAC), dimethyl sufoxide, sulforane, and N-methylpyrrolidone. These solvents may be used as a mixture of two or more thereof.

The copper compound of the formula [III] used for the reaction is in an amount of usually 0.8 to 1.5 times by mole, preferably 1 to 1.2 times by mole, based on the organolithium compound of the formula [II].

The reaction temperature is in the range of from $-120°$ C. to $0°$ C., more preferably approximately $-90°$ C. to $-30°$ C. The reaction time is variable depending upon the reaction time. A reaction time of about one hour at a temperature of $-78°$ C. to $-20°$ C. is usually sufficient.

Preferably, the reaction is carried out in an atmosphere of nitrogen or argon gas.

The thus-obtained reaction product is estimated to have the partial structure represented by the following formula:

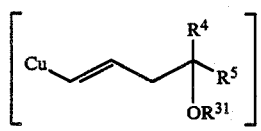

(Tetrahedron Lett., 21, 1247 (1980)).

Then, the above-mentioned reaction product is allowed to react with 4-substituted-2-cyclopentenones of the formula [IV].

The 4-substituted-2-cyclopentenones of the formula [IV] are known materials (U.S. Pat. No. 4,132,726) and are easily available. In the formula, $R^{21}$ is defined as $R^2$ from which a hydrogen atom is removed, as understood from the definition thereof. Examples of $R^{21}$ are the same as described above. With regard to the synthesis of these compounds, reference will be made to a publicttion, Tetrahedron, vol. 32, 1713 (1976).

The reaction with the 4-substituted-2-cyclopentenones of the formula [IV] may be carried out by adding the 4-subsitituted-2-cyclopentenones to the same reaction system without isolating the reaction product after the reaction of the organolithium compound of the formula [II] and the copper compound of the formula [III].

The 4-substituted-2-cyclopentenones are usually used 0.5 to 1.5 times by mole, preferably 0.7 to 1.2 times by mole based on the organolithium compound of the formula [II].

The reaction temperature is $-120°$ C. to $0°$ C., preferably $-90°$ C. to $-30°$ C. The reaction time is variable depending upon the reaction temperature. It is usually 10 minutes to 2 hours.

Preferably, the reaction is carried out in an atmosphere of nitrogen or argon gas.

It is preferable that the reaction be carried out in the presence of, for example, trialkylphosphines such as triethylphosphine and tri-n-butylphosphine, or trialkyl phosphites such as trimethyl phosphite, triethyl phosphite, triisopropyl phosphite and tri-n-butyl phosphite. The use of the tri-n-butylphosphine is especially preferable.

Such trivalent phosphorus compounds may be added during the reaction of the organolithium compound of the formula [II] with the copper compound of the formula [III].

In the process of the present invention, it is estimated that an alkenyl group

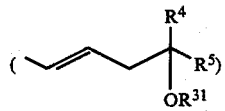

derived from the organolithium compound of the formula is added to the 4-substituted-2-cyclopentenones at the 3-position and an anion is formed at the 2-position thereof so as to produce a so-called conjugated addition enolate. The nitroolefins of the formula [V] are reacted with the conjugated addition enolate to obtain the desired 6-nitroprostaglandins $E_1$.

In the nitroolefins of the formula [V], $R^{11}$ is defined as $R^1$ from which a hydrogen atom and one equivalent cation are removed. Such compounds can be obtained by a method described in Journal of the American Chemical Society, 98, 4679 (1976).

The reaction with the nitroolefins is carried out by adding the nitroolefins of the formula [V] which may be diluted with the above-mentioned non-protonic organic media to the reaction system after the reaction with the 4-substituted-2-cyclopentenones of the formula [IV] is completed.

The nitroolefins is reacted with the enolate formed by conjugation addition is stoichiometrically equimolar amounts. Usually, the enolate is used in an amount of 0.5 to 2.0 moles, more preferably, 0.8 to 1.2 moles, per mole of the 4-substituted-2-cyclopentenones.

The reaction temperature used is in the range of from $-120°$ C. to $0°$ C., preferably from approximately $-90°$ C. to $-30°$ C. The reacion time is variable depending upon the reaction temperature. Usually, an about one hour reaction at a reaction temperature of $-78°$ C. to $-40°$ C. is sufficient. The end point of the reaction is efficiently determined by following the reaction process by a thin layer chromatography, etc.

After the completion of the reaction, the resultant product is isolated from the reaction mixture and refined by a conventional means. For example, extraction, washing, chromatography or combinations thereof is used.

The thus-obtained product then may be optionally subjected to deprotection and/or hydrolysis and/or salt-forming reaction.

The removal of the protective group ($R^{21}$ and/or $R^{31}$) of a hydroxyl group, when the protective group is a group forming an acetal linkage together with an oxygen atom of a hydroxyl group, is conveniently carried out in a reaction solvent such as water, tetrahydrofuran, ethyl ether, dioxane, acetone, and acetonitrile, in the presence of a catalyst such as acetic acid, the pyridinium p-toluenesulfonate or a cation exchange resin. The reaction is usually carried out at a temperature ranging from $-78°$ C. to $+30°$ C. for approximately 10 minutes to 3 days. Where the protective group is a tri ($C_1$–$C_7$) hydrocarbon silyl group, the reaction is carried out in the above-mentioned reaction solvents in the presence of a catalyst such as acetic acid, tetrabutylammonium fluoride, cesium fluoride, hydrofluoric acid, and hydrogen fluoridepyridine at the same temperature for the same period.

The removal of the protective group ($R^{11}$) of a carboxy group, i.e., hydrolysis reaction, is carried out in water or a solvent containing water in the presence of an enzyme such as lipase and esterase at a temperature ranging from $-10°$ C. to $+60°$ C. for approximately 10 minutes to 24 hours.

In accordance with the present invention, the compound containing a carboxyl group produced by the hydrolysis reaction is then optionally subjected to a salt-forming reactin to give the corresponding carboxylic acid salt. The salt-forming reaction is known per se, and is carried out by a neutralization reaction with an inorganic compound, such as potassium hydroxide, sodium hydroxide, and sodium carbonate, or an organic basic compound, such as ammonia, trimethylamine, monoethanolamine, and morpholine, in an amount substantially equal to that of the carboxylic acid according to a conventional method.

Since the production process of the present invention uses a reaction which proceeds stereospecifically, from the starting material having the configuration represented by the formula [II], a compound having the configuration represented by the formula [I] is obtained, and from the enantiomer of the formula [I], an enantiomer of the formula [I] represented by the formula [I'] is obtained.

6-substituted prostaglandins $E_1$ which are compounds of the formula [I-2] in which X in the formula [I] is an oxygen atom and the enantiomers thereof or mixtures thereof in any ratio:

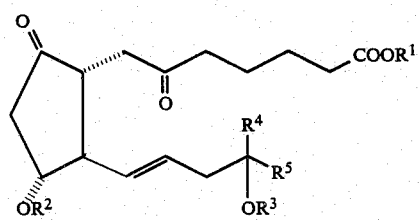

[I-2]

wherein $R^1$, $R^2$, $R^3$, $R^4$ and $R^5$ are the same as defined above, are prepared by converting the nitro group of 6-substituted prostaglandins $E_1$, which are compounds of the formula [I-1] or the enantiomers thereof or mixtures thereof, in any ratio:

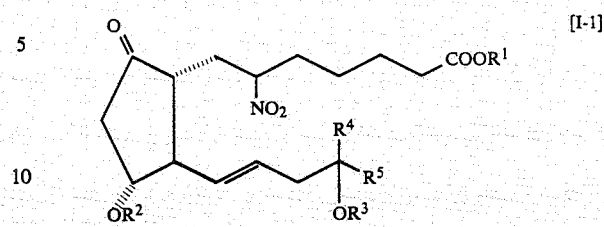

[I-1]

wherein $R^1$, $R^2$, $R^3$, $R^4$ and $R^5$ are the same as defined above, to an oxo group, and then by optionally subjecting the resultant products to deprotection and/or hydrolysis and/or salt-forming reaction.

In the formula, $R^1$, $R^2$, $R^3$, $R^4$ and $R^5$ are the same as defined above and preferably represent the same groups as mentioned above. The 6-substituted prostaglandins $E_1$ of the formula [I-1] used in the process of the present invention may be those obtained according to the above-mentioned method.

The 6-substituted prostaglandins $E_1$ of the formula [I-1] in the process of the present invention have a $\beta$-hydroxycyclopentenone skelton in the molecule thereof and a double bond in the side chain thereof, and thus have the property of being likely to be accompanied by undesirable side reactions under strongly basic conditions, strongly acid conditions, and strongly acidifying conditions. Therefore, the conditions of the nitro group-oxo group conversion reaction become important.

The present inventors made extensive studies into the conditions of the nitro group-oxo group conversion reaction by paying attention to the fact that the nitro group-oxo group conversion reaction has a reaction mechanism wherein the nitro compound becomes the corresponding aci-nitro group intermediate in the presence of a base and thereafter, the intermediate reacts with an acid, a reducing agent or an oxidizing agent to form the corresponding oxo compound. As a result, it was found that the 6-subsituted prostaglandins $E_1$ of the formula [I-1] could be preferably converted to the 6-substituted prostaglandins $E_1$ of the formula [I-2] by reacting the 6-subsituted prostaglandins $E_1$ of the formula [I-1] with an aqueous solution of a trivalent titanium compound to which a buffer salt is added in the presence of a weak basic compound. The reaction conditions will be described hereunder.

The weak basic compounds used herein are preferably those which are weakly reactive to the cyclopentenone skeleton of the formula [I-1] and are capable of withdrawing hydrogen on carbon to which a nitro group is selectively attached. Such weak basic compounds may include, for example, triphenylphosphine, tributylphosphine, tetrabutylammonium fluoride, potassium fluoride, potassium carbonate, tetramethyl guanidine, diisopropylamine, morpholine, pyrrolidne, piperidine, and triethylamine. Triphenylphosphine is especially preferable.

As the trivalent titanium compound, a commercially available aqueous solution of titanium trichloride can be usually used as it is. However, when the aqueous titanium trichloride solution alone is used in the reaction, the reaction system has a pH of 1 or less which provides strongly acidic conditions. Therefore, the use of the aqueous titanium trichloride solution alone is not preferable. For this reason, the abovementioned reaction is usually effected by adding a buffer salt to control the pH to approximately neutrality (pH 4–7, preferably pH about 6). Such buffer salts may include, for example, sodium formate, ammonium acetate, sodium acetate, potassium acetate, sodium acetate, potassium acetate, sodium succinate, sodium citrate, sodium tartrate, sodium phthalate, sodium dihydrogenphosphate, disodium hydrogenphosphate, potassium dihydrogenphosphate, and dipotassium hydrogenphosphate. Ammonium acetate is especially preferable.

The weak basic compound is usually used in an amount of 0.5 20 times by mole, preferably 1 to 10 times by mole, based on the 6-substituted prostaglandins $E_1$ of the formula [I-1] used. The titanium trichloride is usually used in an amount of 1 to 20 times by mole, preferably 2 to 15 times by mole, more preferably 3 to 10 times by mole, based on the 6-substituted prostaglandins $E_1$ of the formula [I-1] used. The amount of buffer salt used is variable depending upon the type thereof and the amount of titanium trichloride used, and is determined by observing the change of the pH. For example, when ammonium acetate is used in an amount of 6 times by mole based on titanium trichloride, the pH of the reaction mixture is adjusted to about 6.

In order that the reaction proceeds smoothly, it is preferable that a relatively water-soluble organic medium be further added to the reaction system. Such organic media may include, for example, ether solvents such as diethyl ether, tetrahydrofuran, dimethoxyethane, and dioxane; and alcohol solvents such as methanol, ethanol, and isopropyl alcohol.

The reaction temperature is usually in the range of from 0° C. to 60° C., preferably from 20° C. to 30° C. The reaction time is variable depending upon the reaction conditions such as the reaction temperature, the amount of the reactants, and the pH. The end point of the reaction is determined by following the reaction according to an analytical means such as a thin layer chromatography. The reaction is terminated at room temperature for 1 to 48 hours.

After the completion of the reaction, the resultant product is isolated from the reaction mixture by a conventional means and refined. For example, extraction, washing, chromatography or combinations thereof may be used.

Thus, the 6-substituted prostaglandins $E_1$ of the formula [I-1] are converted to the 6-substituted prostaglandin $E_1$ of the formula [I-2]. Where the resultant 6-substituted prostaglandins $E_1$ of the formula [I-2] are compounds in which the hydroxyl groups (the 11-position and/or 16-position) and/or the carboxyl group at the 1-position are protected, these compounds are subsequently subjected to deprotection and/or hydrolysis and/or salt formation reaction in a similar manner as mentioned above.

The 6-substituted prostaglandins $E_1$ of the formula [I-2] can be prepared in suite, using the organolithium compound of the formula [II] as the starting material, without once isolating the 6-substituted prostaglandins $E_1$ of the formula [I-1] in the course of the production process. This necessarily provides an industrially advantageous production process.

That is, the above-mentioned process comprises reacting an organolithium compound of the formula [II]:

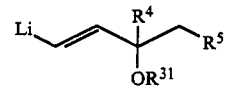

wherein
$R^4$ and $R^5$ are the same as defined above, and $R^{31}$ represents a tri ($C_1$–$C_7$) hydrocarbon silyl group or a group forming an acetal linkage together with an oxygen atom of a hydroxyl group,
with a copper compound of the formula [III]:

$$CuQ \qquad [III]$$

wherein,
Q represents a halogen atom, a cyano group, a phenylthio group or a 1-pentyl group;
then reacting the resultant product with 4-substituted-2-cyclopentenones of the formula [IV]:

wherein
$R^{21}$ represents a tri ($C_1$–$C_7$) hydrocarbon silyl group or a group forming an acetal linkage together with an oxygen atom of a hydroxyl group,
or the enantiomers thereof or mixtures thereof in any ratio; futher reacting the resultant product with nitroolefins of the formula [V]:

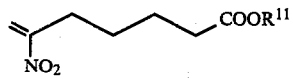

wherein
$R^{11}$ represents a $C_1$–$C_{10}$ alkyl group, a substituted or unsubstituted phenyl group, a substituted or unsubstituted $C_3$–$C_{10}$ cycloalkyl group, or a substituted or unsubstituted phenyl ($C_1$–$C_2$) alkyl group;
then subjecting the reaction mixture to a reaction in which the nitro group is converted to an oxo group without isolating the reaction product; and optionally subjecting the resultant product to deprotetion and/or hydrolysis and/or salt formation reaction. Thus, the 6-substituted prostaglandins $E_1$ of the formula [I-2] are produced.

In the formula, $R^1$, $R^{11}$, $R^2$, $R^{21}$, $R^3$, $R^{31}$, $R^4$, $R^5$, and Q may be those defined above. Until the step of reacting the nitroolefins of the formula [V] is completed, the reaction conditions under which the 6-substituted prostaglandins $E_1$ of the formula [I-1] are prepared can be directly applied.

In the process of the present invention, it is estimated that, as a result of the above-mentioned operations, anenolate in which an alkenyl group, which is the organic group moiety of the organolithium compound, is added to the 4-substituted-2-cyclopentenones at the 3-position and an anion formed at the 2-position is attached to the nitroolefins by a so-called Michael addition and the α-position (the 6-position according to the prostaglandin nomenclature method) of the nitro group becomes an anion, so as to provide a compound in the form of a so-called aci-nitro salt. The greatest feature of the process of the present invention is that the aci-nitro salt intermediate produced according to the above-mentioned two stage reaction (a so-called three component coupling reaction) is directly subjected to the subsequent reaction to convert the nitro group to an oxo group. By carrying out this reaction, it is possible to effect the third stage reaction starting from the organolithium compound without any isolation operation in the course of the reaction process, thereby producing the 6-substituted prostaglandins $E_1$ represented by the formula [I-2] in suite.

Now, a reaction in which the aci-nitro group of the aci-nitro salt intermediate is converted to an oxo group will be described. A reaction wherein a nitro group is converted to an oxo group is known as a Nef reaction, and an aci-nitro group is considered to be an intermediate in this conversion reaction. In the conversion of the 6-substituted prostaglandins $E_1$ represented by the formula [I-1] to the 6-substituted prostaglandins $E_1$ represented by the formula [I-2], mainly the β-hydroxycyclopentenone skeleton in the melecule thereof inhibits the formation of an aci-nitro intermediate. Therefore, a basic material which can be used is limited as described for the above-mentioned production process. In accordance with the process of the present invention, at the conclusion of the two stage reaction, i.e., at the stage before the nitro group-oxo group conversion reaction, the crude reaction product is already an aci-nitro salt intermediate, and an aci-nitro group is not required to intentionally form from a nitro compound and a strongly basic compound as in a conventional Nef reaction. This makes it possible to react the crude reaction product with an acid, a reducing agent or an oxidizing agent.

On the basis of the familiarity and consideration of the above-mentioned two points, the present inventors made extensive studies into overcoming the difficulties associated with the nitro group-oxo group conversion reaction. As a result, it was discovered that, when the reaction mixture obtained after the second stage reaction with the nitroolefins is completed was directly reacted with an acid, a reducing agent or an oxidizing agent under appropriate conditions, the 6-substituted prostaglandins $E_1$ represented by the formula [I-2] could be more conveniently produced. The reaction conditions will be described below.

That is, where an acid is used, an equimolar or more amount of hydrochloric acid (preferably 0.5 to 6 normal, more preferably 1 to 4 normal, hydrochloric acid) or sulfuric acid (preferably 1 to 12 normal, more preferably 3 to 6 normal sulfuric acid) is added to a solution containing an aci-nitro salt intermediate produced by the three component connecting reaction. In order that the reaction proceeds smoothly, it is preferable that a relatively water-soluble organic medium be further added to the reaction system. Such organic media may include, for example, ether solvents such as diethyl ether, tetrahydrofuran, dimethoxyethane and dioxane and alcohol solvents such as methanol, ethanol and isopropyl alcohol.

The reaction temperature is somewhat variable depending upon the type and concentration of the acid used and the type of the water-soluble organic medium. It is usually in the range of from −20° C. to 80° C., preferably from 0° C. to 60° C., more preferably from 20° C. to 50° C. The reaction time is variable depending upon the reaction temperature and the reaction conditions. The end point of the reaction is determined by following the reaction according to an analytical means such as a thin layer chromatography. When the reaction temperature is 40° C., the reaction is terminated after approximately 0.5 to 5 hours.

The method using a reducing agent includes one using an aqueous titanium trichloride solution. This method is carried out according to a method of J. E. McMurry et al. (J. Org. Chem., 38, 4367 (1973), Accounts. Chem. Res., 7, 281 (1974)). That is, an aqueous solution (pH about 6) of titanium trichloride and ammonium acetate in a molar ratio of 1:6 is prepared. This aqueous solution is mixed with a reaction solution containing an aci-nitro salt intermediate produced by the three component coupling reaction. The titanium trichloride is used in an amount of 1 to 20 times by mole, preferably 2 to 15 times by mole, more preferably 3 to 10 times by mole, based on the aci-nitro salt intermediate. In order to ensure that the reaction proceeds smoothly, it is preferable that a relatively water-soluble organic medium be further added to the reaction system. Such organic media may include, for example, ether solvents such as diethyl ether, tetrahydrofuran, dimethoxyethane, and dioxane; alcohol solvents such as methanol, ethanol and isopropyl alcohol; acetone; N,N-dimethylformamide and acetic acid.

The reaction temperature is usually in the range of from 0° C. to 60° C., preferably from 20° C. to 30° C. The reaction time is variable depending upon the reaction conditions such as the reaction temperature, the amount of the reactants, and the pH. The end point of the reaction is determined by following the reaction by means of an analytical means such as a thin layer chromatography. The reaction is terminated at room temperature for 1 to 48 hours.

When an oxidizing agent is used, it is preferable to use, for example, hydrogen peroxide water, tert-butylhydroperoxide, a pyridine-hexamethylphosphoramide complex of molybdenum pentoxide, potassium permanganate, and cerium (IV) ammonium nitrate.

The reaction conditions are variable depending upon the type of the oxidizing agent used. The example, when hydrogen peroxide water is used as an oxidizing agent, hydrogen peroxide water containing hydrogen peroxide in an amount of an equimole or more, preferably 5 to 20 times by mole, based on the used 4-substituted-2-cyclopentenones, preferably 10 to 30% hydrogen peroxide water, is added to a reaction solution containing an aci-nitro salt intermediate produced by reaction with the 4-substituted-2-cyclopentenones of the formula [IV] and then the nitroolefins of the formula [V], so as to effect the reaction. In order to ensure that the reaction proceeds smoothly, it is preferable that a relatively water-soluble organic medium be further added to the reaction system. Such organic media may include, for example, ether solvents such as diethyl ether, tetrahydrofuran, dimethoxyethane, and dioxane, and alcohol solvents such as methanol, ethanol, and isopropyl alcohol.

The reaction temperature is somehat variable depending upon the type and concentration of the water-soluble organic medium used. It is usually in the range of from −20° C. to 80° C., preferably from 0° C. to 50° C., more preferably from 20° C. to 50° C. The reaction time is variable depending upon the reaction temperature and the reaction conditions. The end point of the reaction is determined by following the reaction by an analytical means such as a thin layer chromatography. When the reaction temperature is 40° C., the reaction is terminated in approximately 0.5 to 8 hours.

Where tert-butyl hydroperoxide is used as an oxidizing agent, an equimole or more, preferably 5 to 20 times by mole, of tert-butyl hydroperoxide, based on the used 4-substituted-2-cyclopentenones, is added to the above-mentioned reaction solution containing the aci-nitro salt intermediate, so as to effect the reaction. The completion of this reaction requires the presence of a catalyst. Such catalysts may include, for example, vanadium (IV) oxyacetylacetonato, and molybdenum pentacarbonyl. The catalyst is used in an amount of 0.1 to 20 mol %, preferably 1 to 10 mol %, based on the tert-butyl hydroperoxide.

The reaction temperature is variable depending upon the amount of the tert-butyl hydroperoxide, and the type and amount of the catalyst used. It is usually in the range of from −20° C. to 100° C., preferably from 0° C. to 80° C. The reaction time is variable depending upon the reaction temperature and the reaction conditions. The end point of the reaction is determined by following the reaction by means of an analytical means such as a thin layer chromatography. When the reaction temperature is 40° C., the reaction is terminated in approximately 0.5 to 24 hours.

Oxidizing agents other than the oxidizing agents exemplified herein may include a pyridine-hexamethylphosphoramide complex of molybdenum pentoxide, potassium permanganate (F. T. Williams. Jr. et al., J. Org. Chem., 27, 3699 (1962)), and serium (IV) ammonium nitrate (G. A. Olah et al., Synthesis, 44 (1980); R. C. Cookson et al., Tetrahedron Letters, 23, 3521 (1982)).

After the completion of the reaction, the resultant product is separated from the reaction mixture and refined in a similar manner as described above. For example, extraction, washing, chromatography or combination thereof are used.

Thus, there is obtained a compound of the formula [I-2] in which the hydroxyl group is protected and the carboxylic acid at the 1-position is in the form of an ester. Then, the protective group of the hydroxyl group is removed in a conventional manner to provide a free hydroxyl group, and/or the ester product is subjected to hydrolysis and/or a salt-forming reaction in a similar manner as mentioned above. Thus, the 6-substituted prostaglandins $E_1$ of the formula [I-2] according to the present invention are prepared.

The 6-substituted prostaglandins $E_1$ which are compounds of the formula [I''] produced by the abovementioned process and wherein $R^2$ and $R^3$ in the 6-substituted prestaglandins $E_1$ of the formula [I] are hydrogen atoms:

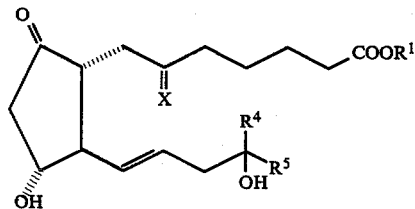

[I'']

wherein $R^1$, $R^4$, $R^5$ and X are the same as defined above, or the enantiomers thereof or mixtures thereof in any ratio can be used for the prevention and/or treatment of digestive organ diseases such as duodenal ulcers and gastric ulcers; liver diseases such as hepatitis, toxipathic hepatitis, fatty liver, hematic coma, hypertrophy of the liver, and hepatocirrhosis; pancreas such as pancreatitis; arinary diseases such as diabetes kidney diseases, acute kidney insufficiency, cystitis, and urethritis; respiratory diseases such as pneumonia and bronchitis; incretion diseases; immunity diseases; toxicores such as alcohol poisoning and carbon tetrachloride poisoning, and low blood pressure. Especially, the 6-substituted prostaglandins $E_1$ of the present invention are useful for the treatment and/or prevention of digestive organ diseases such as duodenal ulcers and gastric ulcers.

Next, to explain the present invention in more detail, examples are given which by no means limit the present invention.

EXAMPLE 1

Synthesis of (16RS)-15-deoxy-11-t-butyldimethylsilyl-16-t-butyldimethylsilyloxy-6-oxoprostaglandin $E_1$ methyl ester A solution of 1.9 M of t-butyllithium in pentane (3.47 ml, 6.6 mmol) was added to a solution of dl-(E)-4-t-butyldimethyl-silyloxy-1-iodo-1-octene (1.22 g, 3.3 mmol) in ether (15 ml) at a temperature of −78° C. and the mixture was stirred for 2 hours. To this solution, a solution of cuprous iodide (630 mg, 3.3 mmol) and tributylphosphine (1.34 g, 6.6 mmol) in ether (5 ml) was added and the mixture stirred at a temperature of −78° C. for 1 hour. To this solution, a solution of (4R)-4-t-butyldimethylsilyloxy-2-cyclopentenone (636 mg, 3.0 mmol) in ether (5 ml) was added and the mixture stirred at a temperature of −78° C. for 15 minutes and then at a temperature of −40° C. for 30 minutes. Then, a solution of methyl-6-nitro-6-heptenoate (617 mg, 3.3 mmol) in ether (5 ml) was added to the above-mentioned solution and the mixture stirred at a temperature of −40° C. for 30 minutes. Furthermore, an aqueous titanium trichloride solution (25%, 22.5 ml. 36 mmol), an aqueous solution of ammonium acetate (16.5 g, 216 mmol) dissolved in 75 ml of water and tetrahydrofuran (150 ml) were added to the above-mentioned solution and the mixture stirred at room temperature for 18 hours. After an aqueous solution of sodium hydrogencarbonate was added to the reaction mixture to neutralize it, the tetrahydrofuran was distilled away under reduced pressure. Hexane was added to the reaction mixtue to extract the organic materials three times. After the resultant extract was washed with an aqueous sodium chloride soluton, was dried over anhydrous magnesium sulfate, and concentrated under reduced pressure to obtain 3.68 g of a crude product. This crude product was subjected to silica gel column chromatography (silica gel 100 g, hexane:ethyl acetate=19:1) to obtain (16RS)-15-deoxy-11-t-butyldimethylsilyl-16-t-butyldimethylsilyloxy-6-oxoprostaglandin $E_1$ methyl ester (843 mg, 1.38 mmol, 46%)

NMR (CDCl$_3$, δ (ppm)); 0.04 (12H, s), 0.85 (21H, s+t), 1.1∼1.9 (10H, m), 1.9∼2.7 (12H, m), 3.61 (3H, s), 3.9∼4.4 (2H, m), 5.3∼5.6 (2H, m).

IR (liquid film, cm$^{-1}$); 1740, 1720, 1255, 1100, 835, 775.

EXAMPLE 2

Synthesis of
(16RS)-15-deoxy-16-hydroxy-6-oxoprostaglandin $E_1$ methyl ester

The (16RS)-15-deoxy-11-t-butyldimethylsilyl-16-t-butyldimethylsilyloxy-6-oxoprostaglandin $E_1$ methyl ester (347 mg, 0.57 mmol) was dissolved in acetonitrile (20 ml), and 0.4 ml of pyridine and then hydorgen fluoride-pyridine (0.8 ml) were added to the resultant solution. The mixure was stirred at room temperature for 2 hours. After an aqueous saturated solution of sodium hydrogencarbonate was added to the reaction mixture to neutralize it, the resultant solution was extracted with ethyl acetate. The resultant organic layer was washed with an aqueous saturated solution of sodium chloride and dried over magnesium sulfate, and was then concentrated under reduced pressure to obtain 255 mg of a crude product. The crude product was subjected to silica gel column chromatography (silica gel 10 g, hexane:ethyl acetate=1:2) to obtain (16RS)-15-deoxy-16-hydroxy-6-oxoprostaglandin $E_1$ methyl ester (190 mg, 0.50 mmol, 87%)

NMR (CDCl$_3$, δ (ppm)); 0.87 (3H, t), 1.1~1.7 (10H, m), 1.9~2.7 (14H, m), 3.61 (3H, s), 3.3~4.3 (2H, m), 5.3~5.6 (2H, m).

IR (liquid film, cm$^{-1}$); 3400, 1740, 1720, 1160, 1080, 970, 730.

MS (20 eV); 364 (M - H$_2$O), 346 (M - 2×H$_2$O).

EXAMPLE 3

Synthesis of
(16RS)-15-deoxy-11-t-butyldimethylsilyl-16-methyl-16-trimethylsilyloxy-6-oxoprostaglandin $E_1$ methylester dl-(E)-4-methyl-4-trimethylsilyloxy-1-iodo-1-octene (1.12 g, 3.3 mmol) was reacted with (4R)-4-t-butyldimethylsilyloxy-2-cyclopentenone (636 mg, 3.0 mmol) and then with methyl-6-nitro-6-heptenoate (617 mg, 3.3 mmol) in exactly the same manner as in Example 1. Subsequently, to the resultant reaction mixture, an aqueous 25% titanium trichloride solution (22.5 ml, 36 mmol), an aqueous solution of ammonium acetate (16.5 g, 216 mmol) in 75 ml of water and tetrahydrofuran (150 ml) were added, and the mixture was stirred at room temperature for 18 hours. After the completion of the reaction, the same post-treatment and column separation as in Example 1 were carried out to obtain (16RS)-15-deoxy-11-t-butyldimethylsilyl-16-methyl-16-trimethylsilyloxy-6-oxoprostaglandin $E_1$ methyl ester (890 mg, 1.53 mmol, 51%).

NMR (CDCl$_3$, δ (ppm)); 0.04 (6H, s), 0.09 (9H, s), 0.85 (12H, s+t), 1.11 (3H, s), 1.1~1.7 (12H, m), 2.0~2.7 (10H, m), 3.60 (3H, s), 3.8~4.2 (1H, m), 5.2~5.6 (2H, m).

IR (liquid film, cm$^{-1}$); 1740, 1720, 1250, 1100, 970, 860, 835, 775, 750.

EXAMPLE 4

Synthesis of
(16RS)-15-deoxy-16-hydroxy-16-methyl-6-oxoprostaglandin $E_1$ methyl ester The (16RS)-15-deoxy-11-t-butyldimethylsilyl-16-methyl-16-trimethylsilyloxy-6-oxoprostaglandin $E_1$ methyl ester (541 mg, 0.93 mmol) obtained in Example 3 according to exactly the same method as in Example 2 was dissolved in acetonitrile (20 ml). To the resultant solution, pyridine (0.4 ml) and hydrogen fluoridepyridine (0.8 ml) were added, and the mixture was reacted at room temperature for 3.5 hours. The same post-treatment and column separation as in Example 2 were carried out to obtain (16RS)-15-deoxy-16-hydroxy-16-methyl-6-oxoprostaglandin $E_1$ methyl ester (298 mg, 0.75 mmol, 81%).

NMR (CDCl$_3$, δ (ppm)); 0.90 (3H, t), 1.13 (3H, s), 1.2~1.7 (10H, m), 2.0~2.8 (14H, m), 3.63 (3H, s), 3.8~4.4 (1H, m), 5.3~5.7 (2H, m).

IR (liquid film, cm$^{-1}$); 3410, 1740, 1720, 1160, 1080, 970, 730.

MS (20 eV); 420 (M - H$_2$O), 402 (M - 2×H$_2$O).

EXAMPLE 5

Synthesis of
(16RS)-15-deoxy-16-hydroxy-16-methyl-6-oxoprostaglandin $E_1$

The (16RS)-15-deoxy-16-hydroxy-16-methyl-6-oxoprostaglandin $E_1$ methyl ester (198 mg, 0.50 mmol) obtained in Example 4 was dissolved in 2 ml of acetone. After a phosphoric acid buffer having a pH of 8 (0.1M, 20 ml) was added to the solution, porcine esterase (produced by Sigma Co., No. E-3128, pH 8, 0.2 ml) was added to the mixture and the resultant mixture stirred at room temperature for 24 hours. At the conclusion of the reaction, the reaction mixture was acidified to a pH of 4 with 0.1N hydrochloric acid and the aqueous layer saturated with ammonium sulfate. Thereafter, the aqueous layer was extracted with ethyl acetate and the extract washed with an aqueous solution of sodium chloride. The washed extract was dried over magnesium sulfate and concentrated under reduced pressure to obtain a crude product. The crude product was subjected to silica gel column chromatography (hexane:ethyl acetate=1:4, 0.1% acetic acid) to refine it, thereby isolating (16RS)-15-deoxy-16-hydroxy-16-methyl-6-oxoprostaglandin $E_1$ (168 mg, 0.44 mmol, 88%).

NMR (CDCl$_3$, δ (ppm)), 0.85 (3H, t), 1.13 (3H, s), 1.1~1.7 (10H, m), 2.1~2.7 (12H, m), 3.8~4.3 (1H, m) 5.3~5.7 (2H, m), 6.13 (3H, bs).

IR (liquid film, cm$^{-1}$); 3400, 1740, 1720, 1710.

EXAMPLE 6

Synthesis of
(16RS)-15-deoxy-11-t-butyldimethylsilyl-16-trimethylsilyloxy-16-vinyl-6-oxoprostaglandin $E_1$ methyl ester dl-(E)-4-trimethylsilyloxy-4-vinyl-1-iodo-1-octene (1.16 g, 3.3 mmol) was reacted with (4R)-4-t-butyldimethylsilyloxy-2-cyclopetenone (636 mg, 30 mmol), then with methyl-6-nitro-6-heptenoate (617 mg, 3.3 mmol), and further with an aqueous solution of titanium trichloride in exactly the same manner as in Example 1. The same post-treatment and column separation as in Example 1 were carried out to obtain (16RS)-15-deoxy-11-t-butyldimethylsilyl-16-trimethylsilyloxy-16-vinyl-6-oxoprostaglandin $E_1$ methyl ester (910 mg, 1.53 mmol, 51%).

NMR (CDCl$_3$, δ (ppm)); 0.04 (6H, s), 0.09 (9H, s), 0.85 (12H, s+t), 1.1~1.7 (12H, m), 2.0~2.7 (10H, m), 3.60 (3H, s), 3.8~4.2 (1H, m), 4.8~5.6 (5H, m).

IR (liquid film, cm$^{-1}$); 3080, 1740, 1720, 1640, 1250, 1100, 970, 860, 835, 775, 750.

EXAMPLE 7

Synthesis of (16RS)-15-deoxy-16-hydroxy-16-vinyl-6-oxoprostaglandin $E_1$ methyl ester The (16RS)-15-deoxy-11-t-butyldimethylsilyl-16-trimethylsilyloxy-16-vinyl-6-oxoprostaglandin $E_1$ methyl ester (594 mg, 1.0 mmol) obtained in Example 6 was dissolved in acetonitrile (20 ml). To this solution, pyridine (0.4 ml) and hydrogen fluoride-pyridine (0.8 ml) were added, and the mixture stirred at room temperature for 2.5 hours. The same post-treatment and column separation as in Example 2 were carried out to obtain (16RS)-15-deoxy-16-hydroxy-16-vinyl-6-oxoprostaglandin $E_1$ methyl ester (306 mg, 0.75 mmol, 75%).

NMR (CDCl$_3$, δ (ppm)); 0.87 (3H, t), 1.2~1.7 (10H, m), 2.0~2.8 (14H, m), 3.60 (3H, s), 3.8~4.4 (1H, m), 4.8~5.7 (5H, m).

IR (liquid film, cm$^{-1}$); 3400, 3080, 1740, 1720, 1640, 1160, 1080, 970, 730.

MS (20 eV) 432 (M - H$_2$O), 414 (M - 2×H$_2$O).

EXAMPLE 8

Synthesis of (16RS)-15-deoxy-11-t-butyldimethylsilyl-16-t-butyldimethylsilyloxy-6-nitroprostaglandin $E_1$ methyl ester In Example 1, the reaction mixture obtained after methyl-6-nitro-6-heptenoate was added was poured into an aqueous solution saturated with ammonium chloride without further treatment with an aqueous titanium trichloride solution, so as to terminate the reaction. After hexane extraction, washing with an aqueous solution of sodium chloride, and drying over magnesium sulfate, concentration under reduced pressure was effected to obtain 4.51 g of a crude product. This crude product was subjected to silica gel column chromatography (silica gel 100 g, hexane:ethyl acetate=19:1) to purity it, thereby obtaining (16RS)-15-deoxy-11-t-butyldimethylsilyl-16-t-butyldimethylsilyloxy-6-nitroprostaglandin $E_1$ methyl ester (1.105 g, 1.72 mmol, 57%).

NMR (CDCl$_3$, δ (ppm)); 0.05 (12H, s), 0.85 (21H, s+t), 1.1~2.6 (22H, m), 3.60 (3H, s), 3.9~4.4 (2H, m), 4.6~5.2 (1H, m), 5.2~5.6 (2H, m).

IR (liquid film, cm$^{-1}$); 1740, 1550, 1255, 1100, 1050, 835, 775.

EXAMPLE 9

Synthesis of (16RS)-15-deoxy-11-t-butyldimethylsilyl-16-methyl-16-trimethylsilyloxy-6-nitroprostaglandin $E_1$ methyl ester In Example 3, the reaction mixture obtained after the addition of 6-nitro-6-heptenoate was subjected to the same post-treatment as in Example 8 without further treatment with titanium trichloride, to obtain (16RS)-15-deoxy-11-t-butyl-dimethylsilyl-16-methyl-16-trimethylsilyloxy-6-nitroprostaglandin $E_1$ methyl ester (56%).

NMR (CDCl$_3$, δ (ppm)); 0.03 (6H, s), 0.10 (9H, s), 0.85 (12H, s+t), 1.16 (3H, s), 1.1~2.6 (22H, m), 3.61 (3H, s), 3.8~4.2 (1H, m), 4.5~5.2 (1H, m), 5.3~5.9 (2H, m).

IR (liquid film, cm$^{-1}$); 1740, 1555, 1250, 1100, 970, 860, 835, 775.

EXAMPLE 10

Synthesis of (16RS)-15-deoxy-11-t-butyldimethylsilyl-16-trimethylsilyloxy-16-vinyl-6-nitroprostaglandin $E_1$ methyl ester In Example 6, the reaction mixture obtained after the addition of 6-nitro-6-heptenoate was subjected to the same post-treatment as in Example 8 without further treatment with titanium trichloride, so as to obtain (16RS)-15-deoxy-11-t-butyldimethylsilyl-16-trimethylsilyloxy-16-vinyl-6-nitroprostaglandin $E_1$ methyl ester (58%).

NMR (CDCl$_3$, δ (ppm)); 0.03 (6H, s), 0.10 (9H, s), 0.85 (12H, s+t), 1.1~2.6 (22H, m), 3.60 (3H, s), 3.8~4.2 (1H, m), 4.5~5.9 (6H, m).

IR (liquid film, cm$^{-1}$); 3080, 1740, 1640, 1555, 1250, 1100, 970, 860, 835, 775.

EXAMPLE 11

Synthesis of (16RS)-15-deoxy-16-hydroxy-6-nitroprostaglandin $E_1$ methyl ester

The compound obtained in Example 8 was treated in acetonitrile with hydrogen fluoride-pyridine in exactly the same manner as in Example 2, followed by the same post-treatment and column separation as in Example 2. Thus, (16RS)-15-deoxy-16-hydroxy-6-nitroprostaglandin $E_1$ methyl ester (89%) was obtained.

NMR (CDCl$_3$, δ (ppm)); 0.89 (3H, t), 1.1~2.7 (24H, m), 3.62 (3H, s), 3.2~4.3 (2H, m), 4.4~5.2 (1H, m), 5.3~5.7 (2H, m).

IR (liquid film, cm$^{-1}$); 3400, 1740, 1550, 1160, 1075, 970, 730.

MS (20 eV); 365 (M - H$_2$O, NO), 349 (M - H$_2$O, NO$_2$), 347 (M - 2H$_2$O, NO), 331 (M - 2H$_2$O, NO$_2$).

EXAMPLE 12

Synthesis of (16RS)-15-deoxy-16-hydroxy-16-methyl-6-nitroprostaglandin $E_1$ methyl ester The compound obtained in Example 9 was treated in acetonitrile with hydrogen fluoride-pyridine in exactly the same manner as in Example 2, followed by the same post-treatment and column separation as in Example 2. Thus, (16RS)-15-deoxy-16-hydroxy-16-methyl-6-nitroprostaglandin $E_1$ methyl ester (68%) was obtained.

NMR (CDCl$_3$, δ (ppm)); 0.88 (3H, t), 1.14 (3H, s), 1.1~2.7 (24H, m), 3.61 (3H, s), 3.7~4.3 (1H, m), 4.4~5.2 (1H, m), 5.2~5.9 (2H, m).

IR (liquid film, cm$^{-1}$); 3400, 1740, 1550, 1160, 1075, 970, 735.

MS (20 eV); 379 (M$^+$-H$_2$O, NO), 363 (M$^+$-H$_2$O, NO$_2$), 361 (M$^+$-2H$_2$O, NO), 345 (M$^-$-H$_2$O, NO$_2$).

EXAMPLE 13

Synthesis of (16RS)-15-deoxy-16-hydroxy-16-vinyl-6-nitroprostaglandin $E_1$ methyl ester The compound obtained in Example 10 was treated in acetonitrile with hydrogen fluoride-pyridine, followed by post-treatment and column separation, in exactly the same manner as in Example 2. Thus, (16RS)-15-deoxy-16-hydroxy-16-vinyl-6-nitroprostaglandin $E_1$ methyl ester (78%) was obtained.

NMR (CDCl$_3$, δ (ppm)); 0.87 (3H, t), 1.1~2.7 (24H, m), 3.60 (3H, s), 3.7~4.3 (1H, m), 4.4~5.9 (6H, m).

IR (liquid film, cm$^{-1}$); 3400, 3080, 1740, 1550, 1460, 1160, 1075, 970, 735.

MS (20 eV); 391 (M$^+$-H$_2$O, NO), 375 (M$^+$-H$_2$O, NO$_2$), 373 (M$^+$-2H$_2$O, NO), 357 (M$^+$-2H$_2$O, NO$_2$).

EXAMPLE 14

Synthesis of
(16RS)-15-deoxy-11-t-butyldimethylsilyl-16-t-butyl-dimethyloxy-6-oxoprostaglandin E$_1$ methyl ester Triphenylphosphine (393 mg, 1.5 mmol) was added to a solution of (16RS)-15-deoxy-11-t-butyldimethylsilyl-16-t-butyldimethylsilyloxy-6-nitroprostaglandin E$_1$ methyl ester (320 mg, 0.50 mmol) obtained in Example 8 in tetrahydrofuran (10 ml). The mixture was stirred at room temperature for 30 minutes. To this mixture, an aqueous 25% titanium trichloride solution (3.1 ml, 50 mmol), an aqueous solution of ammonium acetate (2.31 g, 30 mmol) in 10 ml of water and methanol (20 ml) were added. The resultant mixture was stirred at room temperature for 48 hours. The reaction mixture was neutralized with an aqueous solution saturated with sodium hydrogencarbonate and was extracted with ethyl acetate. The resultant organic layer was washed with an aqueous solution saturated with sodium chloride, dried over magnesium sulfate and concentrated under reduced pressure to obtain a crude product. This crude product was subjected to column chromatography (hexane:ethyl acetate=9:1) to effect separation, thereby obtaining (16RS)-15-deoxy-11-t-butyldimethylsilyl-16-t-butyldimethylsilyloxy-6-oxoprostaglandin E$_1$ methyl ester (128 mg, 0.21 mmol, 42%). The spectral data of this product completely agreed with those of the product obtained in Example 1.

EXAMPLE 15

Synthesis of
(16RS)-15-deoxy-11-t-butyldimethylsilyl-16-methyl-16-trimethylsilyloxy-6-oxoprostaglandin E$_1$ methyl ester From the (16RS)-15-deoxy-11-t-butyldimethylsilyl-16-trimethylsilyloxy-16-vinyl-6-nitroprostaglandin E$_1$ methyl ester obtained in Example 9, (16RS)-15-deoxy-11-t-butyldimethylsilyl-16-trimethylsilyloxy-16-vinyl-6-oxoprostaglandin E$_1$ methyl ester (21%) was obtained in exactly the same manner as in Example 14. The spectral data completely agreed with that of the product obtained in Example 6.

EXAMPLE 16

Synthesis of
(16RS)-15-deoxy-11-t-butyldimethylsilyl-16-trimethylsilyloxy-16-vinyl-6-oxoprostaglandin E$_1$ methyl ester From the (16RS)-15-deoxy-11-t-butyldimethylsilyl-16-trimethylsilyloxy-16-vinyl-6-nitroprostaglandin E$_1$ methyl ester, (16RS)-15-deoxy-11-t-butyldimethylsilyl-16-trimethylsilyloxy-16-vinyl-6-oxoprostaglandin E$_1$ methyl ester (23%) was obtained in exactly the same manner as in Example 14. The spectral data completely agreed with that of the product obtained in Example 6.

EXAMPLE 17

Synthesis of
(16S)-15-deoxy-16-hydroxy-16-methyl-6-oxoprostaglandin E$_1$ methyl ester Exactly the same procedure as in Example 3 was effected except that (1E)-(4S)-4-methyl-4-trimethylsilyloxy-1-iodo-1-octene ($[\alpha]^{24}$+1.6° (C=0.62, CHCl$_3$)) was used in place of the dl-(E)-4-methyl-4-trimethylsilyloxy-1-iodo-1-octene. Thus, (16S)-15-deoxy-11-t-butyldimethylsilyl-16-methyl-16-trimethylsilyloxy-6-oxoprostaglandin E$_1$ methyl ester (64%) was obtained. The spectral data of this product agreed with that of the product of Example 3.

Then, the above-prepared product was subjected to deprotection in exactly the same manner as in Example 4 to obtain (16S)-15-deoxy-16-hydroxy-16-methyl-6-oxoprostaglandin E$_1$ methyl ester (86%). The spectral data of this product agreed with that of the product of Example 4.

EXAMPLE 18

Synthesis of
(16R)-15-deoxy-16-hydroxy-16-methyl-6-oxoprostaglandin E$_1$ methyl ester Exactly the same procedure as in Example 3 was effected except that (1E)-(4R)-4-methyl-4-trimethylsilyloxy-1-iodo-1-octene ($[\alpha]^{24}$−1.6° (C=0.59, CHCl$_3$)) was used in place of the dl-(E)-4-methyl-4-trimethylsilyloxy-1-iodo-1-octene. Thus, (16R)-15-deoxy-11-t-butyldimethylsilyl-16-methyl-16-trimethylsilyloxy-6-oxoprostaglandin E$_1$ methyl ester (62%) was obtained. The spectral data of this product agreed with that of the product of Example 3.

Then, the above-prepared product was subjected to deprotection in exactly the same manner as in Example 4 to obtain (16R)-15-deoxy-16-hydroxy-16-methyl-6-oxoprostaglandin E$_1$ methyl ester (83%). The spectral data of this product agreed with that of the product of Example 4.

EXAMPLE 19

Synthesis of
(16S)-15-deoxy-16-hydroxy-16-methyl-6-nitroprostaglandin E$_1$ methyl ester Exactly the same procedure as in Example 9 was effected except that (1E)-(4S)-4-methyl-4-trimethylsilyloxy-1-iodo-1-octene ($[\alpha]^{24}$+1.6° (C=0.62, CHCl$_2$)) was used in place of the dl-(E)-4-methyl-4-trimethylsilyloxy-1-iodo-1-octene. Thus, (16S)-15-deoxy-11-t-butyldimethylsilyl-16-methyl-16-trimethylsilyloxy-6-nitroprostaglandin E$_1$ methyl ester (57%) was obtained. The spectral data of this product agreed with that of the product of Example 9.

Then, the above-prepared product was subjected to deprotection in exactly the same manner as in Example 12 to obtain (16S)-15-deoxy-16-hydroxy-16-methyl-6-nitroprostaglandin E$_1$ methyl ester (71%). The spectral data of this product agreed with that of the product of Example 12.

EXAMPLE 20

Synthesis of
(16R)-15-deoxy-16-hydroxy-16-methyl-6-nitroprostaglandin E$_1$ methyl ester Exactly the same procedure as in Example 9 was carried out except that (1E)-(4R)-4-methyl-4-trimethylsilyloxy-1-iodo-1-octene ($[\alpha]^{24}$−1.6° (C=0.59, CHCl$_3$)) was used in place of the dl-(E)-4-methyl-4-trimethylsilyloxy-1-iodo-1-octene. Thus, (16R)-15-deoxy-11-t-butyldimethylsilyl-16-methyl-16-trimethylsilyloxy-6-nitroprostaglandin E$_1$ methyl ester (59%) was obtained. The spectral data of this product agreed with that of the product of Example 9.

Then, the above-prepared product was subjected to deprotection in exactly the same manner as in Example 12 to obtain (16R)-15-deoxy-16-hydroxy-16-methyl-6-nitroprostaglandin $E_1$ methyl ester (74%). The spectral data of this product agreed with that of the product of Example 12.

EXAMPLE 21

(i) Determination of Antiulcerative Effect

The inhibiting effect on ulcer formation induced by indomethacin was examined by using rats. Wister male rats (7 weeks old, body weight 220 g) were abstained from food for 24 hours except giving water and then subjected to experiments.

The sample compounds to be tested were dissolved in a phosphoric acid buffer (pH 7.4) containing 0.9% NaCl and the solution was orally administered to the rats. 30 minutes after the administration, indomethacin was orally administered to the rats at a dose of 20 mg/kg. 5 hours after the administration of the indomethacin, the rats were killed and the ulcer formation in the stomach was examined by determining the length of the ulcer formation portion under a stereomicroscope. From this measurement, the inhibition of ulcer formation by the sample compounds was calculated to determine the $ED_{50}$ values. The results are shown in Table 1.

(ii) In vitro PlateletAAggregation Inhibition Effect

The in vitro platelet aggregation inhibition effect of the sample compounds to be tested was examined by using rabbits. That is, blood was collected from the ear vein of native Japanese white male domestic rabbits weighing 2.5 to 3.5 kg. The collected blood was 9 parts by volume per 1 part by volume of a 3.8% sodium citrate solution. The blood was centrifuged at 100 r.p.m. for 10 minutes. The upper layer portion was separated as PRP (rich in platelet blood plasma). The lower layer portion was further centrifuged at 2800 r.p.m. for 10 minutes to divide it into two layers. The upper layer portion was separated as PPP (poor in platelet blood plasma). The member of the platelet was diluted with PPP to 6 to $7 \times 10^7/\mu l$. After the adjustment, 25 $\mu l$ of the sample compound was added to 250 $\mu l$ of PRP, which was preincubated at a temperature of 37° C. for 2 minutes. Thereafter, 10 $\mu M$ of ADP (final) was added to the preincubated PRP to record the variation of the transmittance by means of aggregometer. The sample compounds were dissolved in ethanol to provide 10 mg/ml.

When the activity of the sample compounds was determined, the ethanol solution was diluted with a phosphoric acid buffer (pH 7.4). The ethanol solution diluted with the buffer was left to stand at a temperature of 0° C. for 4 hours, after which the activity of the sample compounds was determined in the same manner.

The agglutination inhibition was calculated by the following formula:

$$\text{Inhibition (\%)} = \left(1 - \frac{T}{T_0}\right) \times 100$$

$T_0$: the transmittance of the system to which the phosphoric acid buffer is added.

$T$: the transmittance of the system to which the sample compounds are added.

The lowest concentration of the sample compounds at which the inhibition is 50% was represented as in $IC_{50}$ value. The results are shown in Table 1.

TABLE 1

| Compound | Antiulcerative effect $ED_{50}(\mu g/kg)$P.O. | Anti-platelet aggregation effect $IC_{50}(\mu g/ml)$ |
|---|---|---|
| Compound of this invention | 22 | 100< |
| Comparative compound | 100< | 1.2 |

As in apparent from Table 1, the compounds of the present invention are those having especially strong antiulcerative effect.

CAPABILITY OF EXPLOITATION IN INDUSTRY

The 6-substituted prostaglandins $E_1$ of the present invention can be used for the prevention and treatment of various diseases such as digestive organ diseases, e.g., duodenal ulcers and gastric ulcers; liver diseases, e.g., hepatitis, toxipathic hepatitis, fatty liver, hepatic coma, hepertrophy of the liver, and hepatocirrhosis; pancreas, e.g., pancreatitis; arinary diseases, e.g., diabetes kidney diseases, acute kidney insufficiency, cystitis, and urethritis; respiratory diseases, e.g., pneumonia and bronchitis; incretion diseases; immunity diseases; toxicoses, e.g., alcohol poisoning and carbon tetrachloride poisoning and low blood pressure. The 6-substituted prostaglandins $E_1$ of the present invention are especially useful for the treatment and/or prevention of digestive organ diseases such as duodenal ulcers and gastric ulcers.

We claim:

1. 6-Substituted prostaglandins $E_1$ which are compounds represented by the following formula [I] or their enantiomers or mixtures thereof in any ratio:

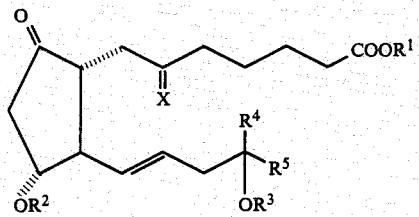

wherein $R^1$ represents a hydrogen atom, a $C_1$-$C_{10}$ alkyl group, a substituted or unsubstituted phenyl group, a substituted or unsubstituted $C_3$-$C_{10}$ cyloalkyl group, a substituted or unsubstituted phenyl ($C_1$-$C_2$) alkyl group, or one equivalent cation;

$R^2$ and $R^3$, which may be the same or different, represent a hydrogen atom, a tri ($C_1$-$C_7$) hydrocarbon silyl group, or a group forming an acetal linkage together with an oxygen atom of a hydroxyl group;

$R^4$ represents a hydrogen atom, a methyl group or a vinyl group;

$R^5$ represents a linear or branched $C_3$-$C_8$ alkyl group, a linear or brancehd $C_3$-$C_8$ alkenyl group, a linear or branched $C_3$-$C_8$ alkynyl group, a phenyl group which is unstubstituted or substituted, a $C_3$-$C_{10}$ cycloalkyl group which is unsubstituted or substituted, or a linear or branched $C_1$-$C_5$ alkyl group which is substituted with a $C_1$-$C_6$ alkoxy group, a phenyl group which is unsubstituted or substituted, a phenoxy group which is unsubstituted or substituted, or a $C_3$-$C_{10}$ cycloalkyl group which is unsubstituted or substituted;

X represents an

group or an oxygen atom, and said substituted groups are independently substituted with a $C_2$-$C_7$ acyloxy group, a $C_1$-$C_4$ alkyl group which is unsubstituted or substituted with a halogen atom, a $C_1$-$C_4$ alkoxy group which is unsubstituted or substituted with a halogen atom, a nitrile group, a carboxyl group or a ($C_1$-$C_6$) alkoxycarbonyl group.

2. The 6-substituted prostaglandine $E_1$ according to claim 1, wherein $R^1$ is a hydrogen atom, a $C_1$-$C_{10}$ alkyl group or an equivalent cation.

3. The 6-substituted prostaglandine $E_1$ according to claim 1, wherein $R^2$ and $R^3$ may be the same or different and are a hydrogen atom, a tri ($C_1$-$C_4$) alkylsilyl group, a diphenyl ($C_1$-$C_4$) alkylsilyl group, a 2-tetrahydropyranyl group, a 2-tetrahydrofuranly group, a 1-ethoxyethyl group, a 2-ethoxy-2-propyl group, a (2-methoxyethoxy) methyl group, or a 6,6-dimethyl-3-oxa-2-oxobicyclo [3,1,0] hex-4-yl group.

4. The 6-substituted prostaglandins $E_1$ according to claim 1, wherein $R^5$ is a butyl group, a pentyl group, a 1-methyl-1-butyl group, a 2-methyl-1-butyl group, a cyclopentyl group, a cycloshexyl group, or a phenyl group.

* * * * *